(12) United States Patent
Brady et al.

(10) Patent No.: US 9,179,849 B1
(45) Date of Patent: Nov. 10, 2015

(54) MOBILE PLETHYSMOGRAPHIC DEVICE

(71) Applicant: Impact Sports Technologies, Inc., Las Vegas, NV (US)

(72) Inventors: Donald Brady, Las Vegas, NV (US); Nikolai Rulkov, San Diego, CA (US); Mark Hunt, San Diego, CA (US)

(73) Assignee: Impact Sports Technologies, Inc., Las Vegas, NV (US)

( * ) Notice: Subject to any disclaimer, the term of this patent is extended or adjusted under 35 U.S.C. 154(b) by 0 days.

(21) Appl. No.: 14/642,604

(22) Filed: Mar. 9, 2015

Related U.S. Application Data

(63) Continuation-in-part of application No. 14/485,770, filed on Sep. 14, 2014, now Pat. No. 8,974,396.

(60) Provisional application No. 62/028,811, filed on Jul. 25, 2014.

(51) Int. Cl.
*A61N 1/00* (2006.01)
*A61B 5/024* (2006.01)
*A61B 5/00* (2006.01)

(52) U.S. Cl.
CPC .......... *A61B 5/02427* (2013.01); *A61B 5/0022* (2013.01); *A61B 5/6824* (2013.01); *A61B 5/721* (2013.01)

(58) Field of Classification Search
CPC .................................................. A61B 5/0452
USPC ................................. 600/508, 536
See application file for complete search history.

(56) References Cited

U.S. PATENT DOCUMENTS

| | | | |
|---|---|---|---|
| 6,551,252 B2 * | 4/2003 | Sackner et al. | 600/536 |
| 6,758,820 B2 | 7/2004 | Narimatsu et al. | |
| 8,755,871 B2 | 6/2014 | Weng et al. | |
| 8,768,438 B2 | 7/2014 | Mestha et al. | |
| 2011/0004072 A1 | 1/2011 | Fletcher et al. | |
| 2012/0310100 A1 | 12/2012 | Galen et al. | |
| 2013/0138002 A1 * | 5/2013 | Weng et al. | 600/508 |

OTHER PUBLICATIONS

Allen et al., Photoplethysmogrpahy dettection of lower limb peripheral arterial occulisive disease: a comparison of pulse timing, amplitude and shape charateristics, Institute of Physics Publishing, Physiological Measurement 26, 811-821 (Jul. 6, 2005).
U.S. Appl. No. 14/542,632, filed Nov. 16, 2014, Office Action dated Apr. 16, 2015.

* cited by examiner

*Primary Examiner* — Nicole F Lavert
*Assistant Examiner* — Nadia A Mahmood
(74) *Attorney, Agent, or Firm* — Clause Eight IPS; Michael Catania

(57) ABSTRACT

A mobile plethysmographic device for detecting a premature ventricular contraction event is disclosed herein. The mobile plethysmographic device generates a pleth waveform, which is automatically screened by algorithms that measure the waveform to correlate, detect and store aberrations related to heart anomalies. A premature ventricular contraction event for a patient is determined based on an identification of a time interval of the pleth waveform that is below the threshold minimum time interval followed immediately by a time interval that is above the threshold maximum tine interval.

12 Claims, 9 Drawing Sheets

MOBILE PLETHYSMOGRAPHIC DEVICE

CROSS REFERENCES TO RELATED APPLICATIONS

The Present Application is a continuation-in-part application of U.S. patent application Ser. No. 14/485,770, filed on Sep. 14, 2014, now U.S. Pat. No. 8,974,396, issued on Mar. 10, 2015, and claims priority to U.S. Provisional Patent Application No. 62/028,811, filed on Jul. 25, 2014, both of which are hereby incorporated by reference in their entireties.

STATEMENT REGARDING FEDERALLY SPONSORED RESEARCH OR DEVELOPMENT

Not Applicable

BACKGROUND OF THE INVENTION

1. Field of the Invention

The present invention is related to plethysmographic devices. More specifically, the present invention relates to a method for determining a premature ventricular contraction event using a mobile plethysmographic device.

2. Description of the Related Art

There is no easy method to determine if someone is suffering from a peripheral artery disease.

Peripheral artery disease is often associated with high blood pressure, diabetes, heart disease, stroke, sedentary lifestyle and aging—cholesterol and fat plaque blocks circulation to vital arteries, often in the legs and feet. Diagnosis for Peripheral Artery Disease ("PAD") is typically done by comparing results from two blood pressure cuffs. To help determine how well a patient's blood is flowing, experienced clinicians use the ankle-brachial index, a painless, inexpensive exam, to compare blood pressure in a patient's feet to the blood pressure in his arms. Particularly lower-leg pain, is misdiagnosed and primary care doctors make referrals to orthopedic surgeons, nerve specialists and podiatrists.

Arrhythmias are caused by problems with the heart's electrical system. An arrhythmia is a heartbeat that's too fast, too slow or irregular (uneven). The electrical signals may fire too fast (tachycardia) or too slowly (bradycardia), or in an uneven (irregular) way. When you have an arrhythmia, your heart may seem to skip beats or flutter. Fibrillation is an abnormal firing of signals within an area of the heart causing a disorganized beat. Abnormal electrical signals can originate in different areas of the heart (such as the atria or ventricles) causing arrhythmias.

Tachycardia is a heart rate that exceeds the normal range. In general, a resting heart rate over 100 beats per minute is accepted as tachycardia. Tachycardia can be caused by various factors that often are benign. However, tachycardia can be dangerous, depending on the speed and type of rhythm.

Bradycardia is the resting heart rate of under 60 beats per minute ("BPM"), although it is seldom symptomatic until the rate drops below 50 BPM. It sometimes results in fatigue, weakness, dizziness, and at very low rates fainting. A waking heart rate below 40 BPM is considered absolute bradycardia.

Sinus arrhythmia involves cyclic changes in the heart rate during breathing. It is very common in children and often found in young adults. Patients with sinus arrhythmia do not experience any cardiovascular symptoms. The sinus node rate can change with inspiration/expiration, especially in younger people. The heart rate speeds up with inspiration (since it inhibits your vagal nerve) and decreases with expiration (stimulates your vagal nerve). Sick sinus syndrome (SSS) occurs when over time the sinus node scars and becomes replaced with fibrous tissues. SSS contains a spectrum of arrhythmias including severe sinus bradycardia, tachycardic-bradycardic syndrome (tachy-brady syndrome), or sinus exit block/sinus pauses. Also known as "tachy-brady syndrome," sick sinus syndrome is a common condition that affects the elderly, accounting for the majority of patients undergoing pacemaker implantation in the U.S.

Premature Atrial Contractions (PACs) are amongst the most common forms of arrhythmias. It is due to the premature discharge of an electrical impulse in the atrium, causing a premature contraction. A PAC is premature, because it occurs earlier than the next regular beat should have occurred.

Premature ventricular contractions (PVCs) are premature heartbeats originating from the ventricles of the heart. Premature ventricular contractions are premature because they occur before the regular heartbeat.

In atrial fibrillation, the normal regular electrical impulses generated by the sinoatrial node in the right atrium of the heart are overwhelmed by disorganized electrical impulses usually originating in the roots of the pulmonary veins. This leads to irregular conduction of ventricular impulses that generate the heartbeat. AF may occur in episodes lasting from minutes to days (paroxysmal AF) or may be permanent in nature. Many medical conditions increase the risk of AF, in particular mitral stenosis (narrowing of the mitral valve of the heart).

The prior art requires ECG devices attached to a patient in order to determine if a PAC event is occurring. Due to all of this effort required to determine if a PAC event using the ECG device, most patients fail to get diagnosed. Thus, there is a need for a mobile plethysmographic device that can be worn for an extended period and provide PAC information to a user.

BRIEF SUMMARY OF THE INVENTION

The present invention is a mobile plethysmographic device worn on the arm or wrist that continuously monitors heart rate on a beat to beat basis to screen for anomalies such as but not limited to Premature Ventricular Contractions ("PVC"), Premature Arial Contractions ("PAC") and Heart Arrhythmias, Tachycardia or Bradycardia. The mobile plethysmographic device generates a photoplethysmograph ("PPG") signal, also referred to as a pleth waveform, which is analyzed for anomalies. The mobile plethysmographic device uses an integrated accelerometer to validate the accuracy of the pleth waveform by detecting motion that is disturbing and corrupting the pleth waveform or to indicate a stable measurement with no motion to validate the waveform data with a high degree of confidence. The pleth waveforms are directly correlated to various heart anomalies and used as a simple, accurate, and convenient means of screening patients for heart conditions. The pleth waveform data is automatically screened by algorithms that measure the waveform to correlate, detect and store aberrations related to heart anomalies. The mobile plethysmographic also permits the wearer to send a manual command to the mobile plethysmographic device to store data if the wearer senses an event is occurring. The mobile plethysmographic device is preferably worn continuously, including during sleep to monitor, screen and store heart rate data. The mobile plethysmographic device is also used to screen for heart conditions related to sleep apnea.

The mobile plethysmographic device has the capability to store onboard heart rate data and the capability to download data for further review via Bluetooth, Bluetooth Low Energy, ANT, 802.11 protocols or other similar wireless data transfer means. The mobile plethysmographic device also has the means to transfer data via a USB using a wired interface from the mobile plethysmographic device to any USB host capable device.

One aspect of the present invention is a method for determining a premature ventricular contraction (PVC) event for a patient. The method comprises generating a plethysmographic waveform for a patient from a digitized electrical signal generated by an optical sensor controlled by a processor that acquires the waveform data and processes it. The optical sensor, the analog front-end (AFE) for sensor signal conditioning and the processor are on a mobile device. The plethysmographic signal comprises a plurality of pulse waves. The method steps are done at the processor on the mobile device.

Another aspect of the present invention is a method for determining a premature ventricular contraction event for a patient by first measuring a plethysmographic signal for a patient from an optical signal generated by an optical sensor and digitized and processed by a processor, the optical sensor and processor on a mobile device, the plethysmographic signal comprising a plurality of pulse waves. Next, at the processor a maximum peak value for each pulse wave of the plurality of pulse waves of the plethysmographic signal is identified to generate a plurality of maximum values of the plethysmographic signal. Next, time intervals between adjacent maximum values of the plethysmographic signal are calculated at the processor. Next, a threshold minimum time interval and a threshold maximum time interval for the plurality of time intervals are established at the processor. Finally, a premature ventricular contraction event for the patient is determined at the processor based on an identification of a time interval that is below the threshold minimum time interval followed immediately by a time interval that is above the threshold maximum tine interval.

The method includes identifying a peak value and its time of occurrence for each cardiac cycle of the plurality of pulse waves of the plethysmographic signal to generate a plurality of maximum waveform values and event times. This is preferably done for each cycle of the plethysmographic signal.

The method further includes calculating time intervals between maximum peak values of adjacent cardiac cycles. The cardiac cycles are from continuously acquired plethysmographic data.

The method further includes calculating a plurality of variations between adjacent time intervals.

The method further includes calculating differences between peak values of adjacent cardiac cycles.

The method further includes establishing threshold values for allowed (typical) variations between adjacent cardiac cycles. The allowed variations are from time intervals and peak values.

The method further includes determining a premature ventricular contraction (PVC) event for the patient based on an identifying a time interval and peak value changes that exceed corresponding threshold values.

The method further includes validating detected PVC events.

The method preferably comprises recording the PVC event as a first PVC event in a memory of the mobile device.

The method further comprises using three axis accelerometer information to validate PVC events by measuring motion activity and verifying the validity of the PVC event when the motion measured by the accelerometer remains less than a preset threshold.

The method preferably further comprises transmitting the PVC event information from the mobile device to a processing device using a transceiver on the mobile device.

Having briefly described the present invention, the above and further objects, features and advantages thereof will be recognized by those skilled in the pertinent art from the following detailed description of the invention when taken in conjunction with the accompanying drawings.

DETAILED DESCRIPTION OF THE INVENTION

Figure 1:
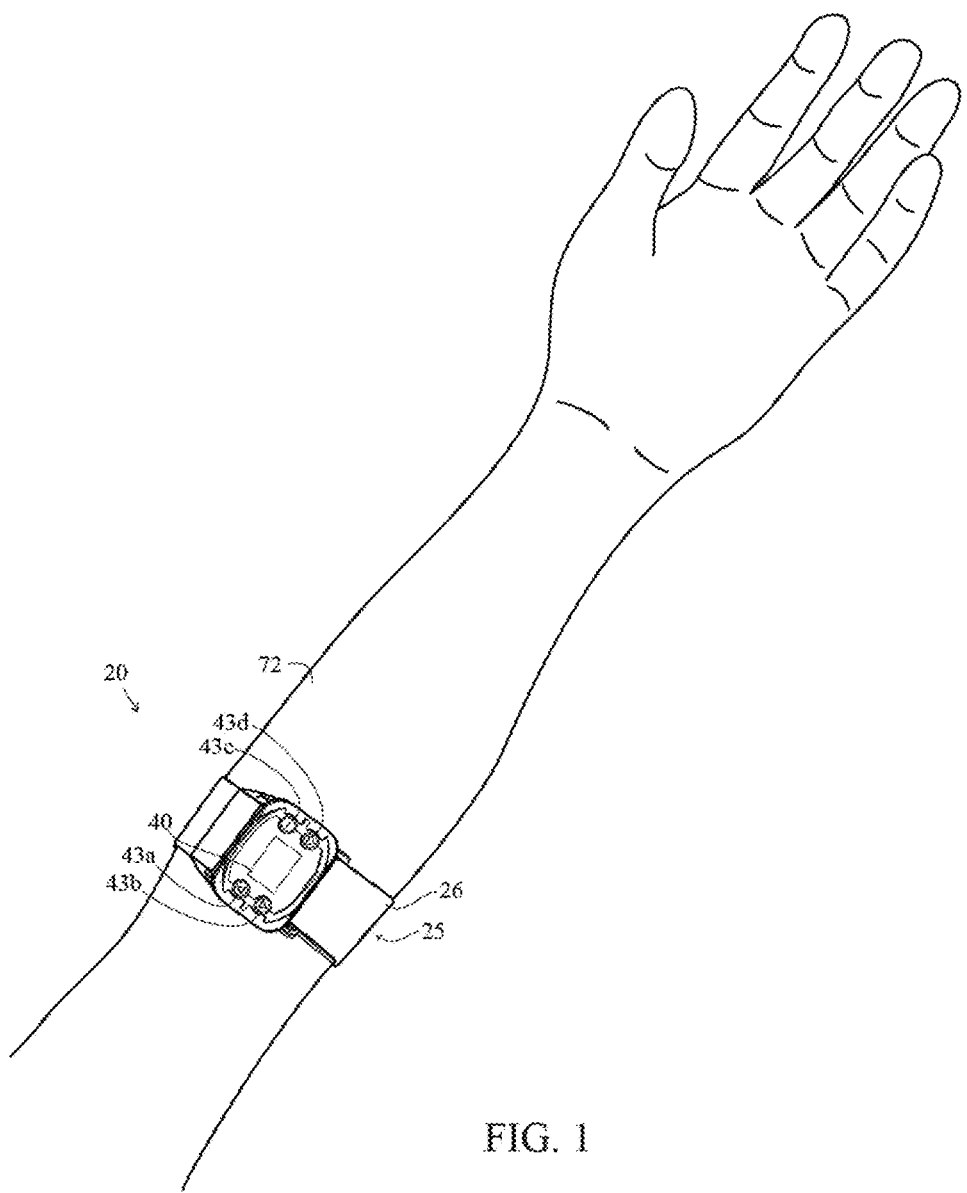
FIG. 1 is a plan view of a preferred embodiment of a mobile plethysmographic device worn by a user.
Figure 2:
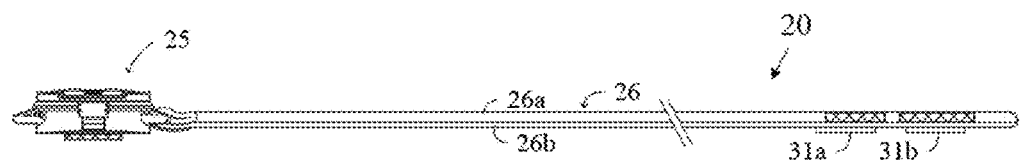
FIG. 2 is a side view of a mobile plethysmographic device.
Figure 3:
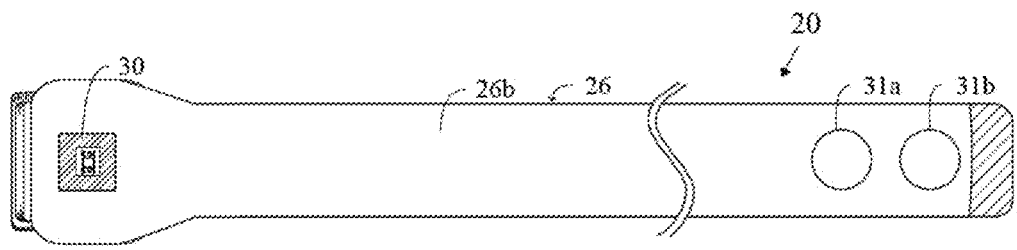
FIG. 3 is an interior surface plan view of a mobile plethysmographic device.
Figure 4:
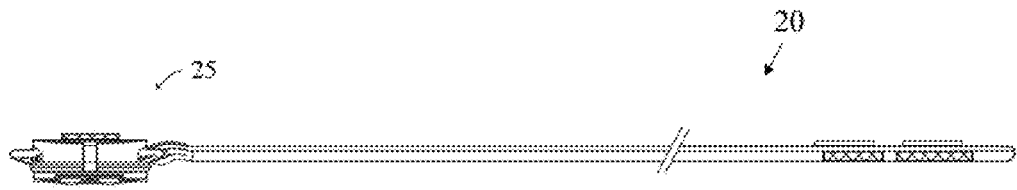
FIG. 4 is a side view of a mobile plethysmographic device.
Figure 5:
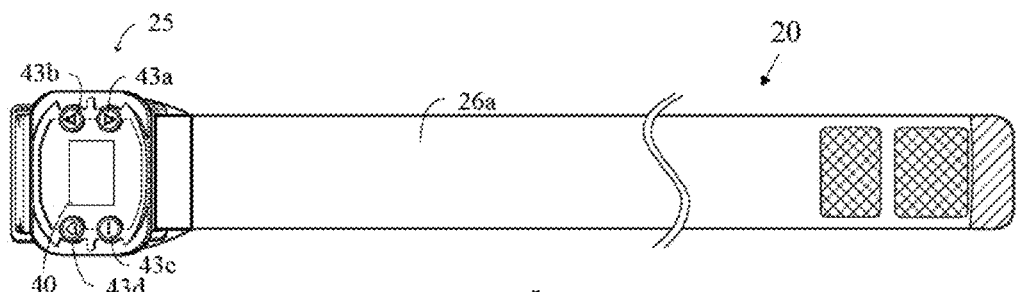
FIG. 5 is an exterior surface view of a mobile plethysmographic device.

As shown in FIGS. 1-5, a mobile plethysmographic device is generally designated 20. The mobile plethysmographic device 20 preferably includes an article 25 and an attachment band 26 having an exterior surface 26a and interior surface 26b. The mobile plethysmographic device 20 is preferably secured with VELCRO® hook and loop material 31a and 31b. The article 25 preferably includes an optical sensor 30, control components 43a-43c and optionally a display member 40. The mobile plethysmographic device 20 is preferably worn on a user's wrist, arm 72 or ankle.

The article 25 preferably has a USB port for a wired connection to a computer, tablet, video monitor or mobile communication device such as smartphone.

It is desirous to adapt the mobile plethysmographic device 20 to the anatomy of the user's arm 72 or even the user's ankle. The band 26 is preferably composed of neoprene, leather, synthetic leather, LYCRA, another similar material, or a combination thereof. The article 25 is preferably composed of a semi-rigid or rigid plastic with a rubber-like or semi-flex plastic bottom layer for contact with the user's body. The bottom layer of the article 25 may have a curved surface for contact with a user's body. The article 25 preferably has a mass ranging from 5 grams to 50 grams. Preferably, the lower the mass of the article 25, the more comfort to the user. The article 25 preferably has a thickness ranging from 5 mm to 10 mm, and is most preferably 6.5 mm.

Although the mobile plethysmographic device 20 is described in reference to an article worn on a user's arm, wrist or ankle, those skilled in the pertinent art will recognize that the mobile plethysmographic device 20 may take other forms such as eyewear disclosed in Brady et al, U.S. Pat. No. 7,648,463, for a Mobile plethysmographic device, Method And System, which is hereby incorporated by reference in its entirety or a glove such as disclosed in Rulkov et al., U.S. Pat. No. 7,887,492, for a Mobile plethysmographic device, Method And System, which is hereby incorporated by reference in its entirety.

Figure 6:
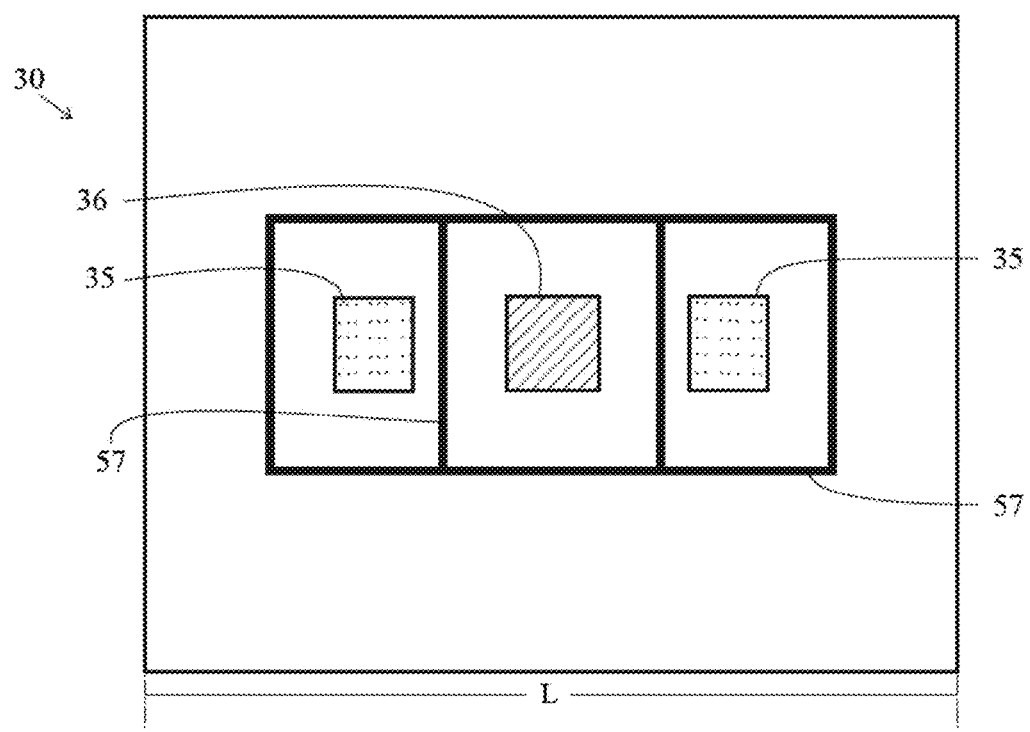
FIG. 6 is an isolated view of the electrical components of a mobile plethysmographic device.
Figure 7:
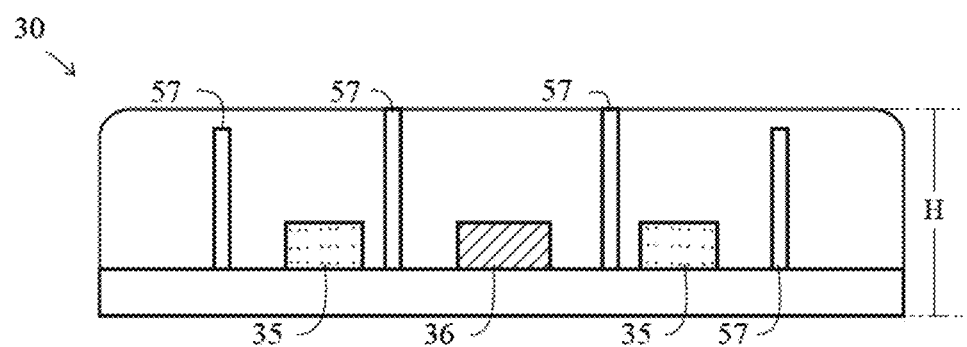
FIG. 7 is isolated side view of the electrical components of a mobile plethysmographic device.
Figure 8:
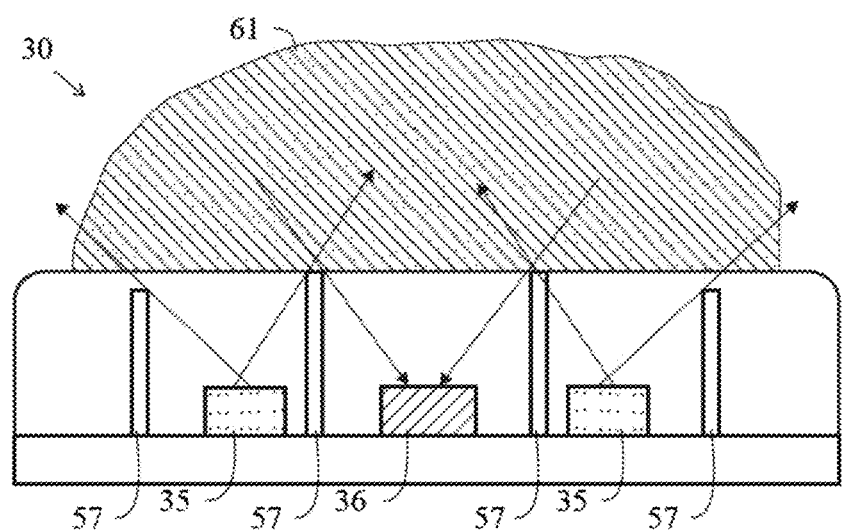
FIG. 8 is an isolated exterior surface view of an optical sensor for a mobile plethysmographic device.

FIGS. 6-8 illustrate the sensor 30. The sensor 30 has a photodetector 36, at least two LEDs 35 and an opaque light shield 57. The LEDs 35 are preferably green light LEDs of the same wavelength. The sensor 30 preferably has a length, L, of 7-10 mm on each side, as shown in FIG. 6. The sensor 30 preferably has a height, H, of 1-1.5 mm, as shown in FIG. 7. The opaque light shield 57 blocks the direct light from the LEDs 35 to the photodetector 36. Only the green light diffused through the translucent media (skin of the user) 61, as shown in FIG. 8, is allowed to enter the chamber of the photodetector 36. This provides for a more accurate heart rate or vital sign signal. The use of two green LEDs form symmetric light diffusion volume around the sensor. The use of two green LEDs also mitigates mechanical noise.

In a preferred design of the sensor 30, the distance between the centers of active areas of LEDs 35 is preferably 5-6 mm. The active area (photodetector 36) of a sensor 30 is placed in the middle of that distance. In the custom sensor, the distance of a custom sensor is preferably in the range of 3-4 mm (which means the spacing between the centers of photodetector 36 and LEDs 35 is about 1.5-2 mm). The distance is preferably sufficient for the placement of an opaque barrier between them. To control the amplitude of the LED intensity pulse a sufficient current (voltage) range of intensity ramp is used to control the LEDs 35 and to achieve the same levels of intensity in both LEDs 35 within a given range. The electrical characteristics of 520 nm LED in terms of voltage range for intensity ramp is sufficient. The top surface of the sensor 30 is preferably flat and in steady contact with the skin. Under a strong motion condition, the skin moves at the border of the contact surface. The sizes of the sensor area and flat skin contact area are selected to reduce the boundary motion effects. If the distance between the LEDs and sensor is reduced, a lighted area of the skin is smaller, and the contact area is reduced (5×5 mm is acceptable). A non allergenic epoxy is an easy way to seal the contact area from moisture. The preferred embodiment uses a fixed pulse width within the range of 125 to 250 microseconds (μsec) turning on LEDs periodically with period two msec and a TSL13T photodetector 36. The output signal of the sensor 30 is monitored to ensure that it is not saturated. The use of short-term LED pulses combined with a high pass filter to reduce ambient light effects. In the preferred embodiment, voltage is collected at the sensor output every two msec synchronously with the LED pulse. The microprocessor, averages eight consecutive samples in order to improve the SNR (signal to noise ratio) and then works with the averaged numbers. Therefore the sampling rate for raw data is preferably two msec, however if eight-sample averaging is utilized in the integrated sensor the data output rate is reduced to sending a new averaged value every sixteen msec. An ADC with at least 12-bit resolution is used. The response of TSL13T photodiode (from AMS-TAOS USA INC., of Plano Tex.) is acceptable. The detailed description of the sensor and front-end design along with signal processing method is disclosed in U.S. Pat. No. 8,460,199B2, which is hereby incorporated by reference in its entirety.

The optical sensor 30 of the mobile plethysmographic device 20 is preferably worn on the user's arm 72, wrist or ankle. However, those skilled in the pertinent art will recognize that the plethysmographic optical sensor may be placed elsewhere on the body of the user without departing from the scope and spirit of the present invention. In a preferred embodiment, the optical sensor 30 is a plurality of light emitting diodes ("LED") 35, as shown in FIGS. 6-8, based on green light (wavelength of 500-570 nm), wherein the LEDs 35 generate green light, preferably at wavelength of 520 nm, and a phtotodetector 36 detects the green light. Yet in an alternative embodiment, the optical sensor 30 is a photodetector 36 and a single LED 35 transmitting light at a wavelength of approximately 900 nanometers as a pulsed infrared LED. As the heart pumps blood through the arteries in the user's arm, ankle or wrist, the photodetector 36, which is typically a photodiode, detects reflectance/transmission at the wavelengths (green, red or infrared), and in response generates a radiation-induced signal.

A preferred optical sensor 30 utilizing green light is a TSL13T light to voltage converter sensor from AMS-TAOS USA INC., of Plano Tex. Output voltage is linear with light intensity (irradiance) incident.

Figure 9:
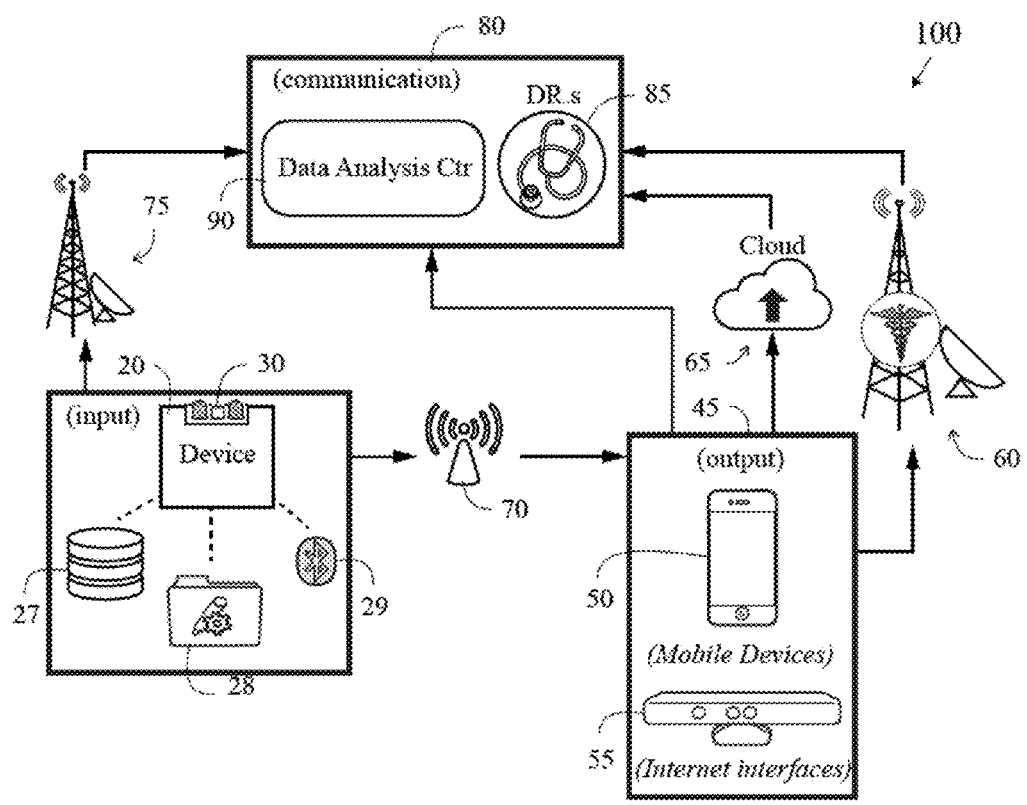
FIG. 9 is a block diagram of a system for detecting PVC events utilizing a mobile plethysmographic device.

FIG. 9 shows a system 100 for detecting PAC events utilizing a mobile plethysmographic device. The mobile plethysmographic device 20 comprises an optical sensor 30, BLUETOOTH 29 or wireless radio, an application 28, and memory or a database 27. Using BLUETOOTH or a wireless network 70, the mobile plethysmographic device 20 sends data to output devices 45 such as a mobile smartphone 50 or an interactive gaming device 55. The data is then sent to a secondary communication node 80, such as to a data analysis center 90 or to a doctor's office 85, via a private cloud (server) 65 or through a dedicated medical communication network 60. If the mobile plethysmographic device 20 is equipped with a transceiver then data can be sent directly through a cellular network 75 to a secondary communication node 80.

In one embodiment, discussed below, the display member 40 is removed and the signal is sent to an output device 45 such as a personal digital assistant, laptop computer, mobile telephone 50, exercise equipment, gaming device 55, or the like for display and even processing of the user's real-time vital signs information, as shown in FIG. 9. Alternatively, the circuitry assembly includes a flexible microprocessor board which is a low power, micro-size easily integrated board which provides blood oxygenation level, pulse rate (heart rate), signal strength bar graph, plethysmogram and status bits data. The microprocessor can also store data. The microprocessor processes the data to display pulse rate, blood oxygenation levels, calories expended by the user of a pre-set time period, target zone activity and time. The display member 40 is preferably an Organic Light Emitting Diode (OLED) array. Alternatively, the display member 40 is a liquid crystal display ("LCD") or other similar display device or a Light Emitting Diode (LED).

A microprocessor processes the signal generated from the optical sensor 30 to generate the pleth waveform for the user, which is displayed on the display member 40. The control components 43a-c are connected to the processor to control the input of information and the output of information displayed on the display member 40.

The mobile plethysmographic device 20 is preferably powered by a power source positioned on the article 25. Preferably the power source is a battery. The power source is preferably a lithium ion rechargeable battery such as available from NEC-Tokin. The power source preferably has an accessible port for recharging. The circuit assembly of the mobile plethysmographic device preferably operates in a range of 3.5-5 volts and draws a current of 20- to 40 milliamps. An alternative power source is an AA or AAA disposable or rechargeable battery. The power source preferably provides at least 900 milliamp hours of power to the mobile plethysmographic device 20.

The mobile plethysmographic device 20 alternatively has a short-range wireless transceiver 29, which is preferably a transmitter operating on a wireless protocol, e.g. BLUETOOTH, part-15, or 802.11. "Part-15" refers to a conventional low-power, short-range wireless protocol, such as that used in cordless telephones. Other communication protocols include a part 15 low power short-range radio, standard BLUETOOTH or BLUETOOTH Low Energy (to conserve power) or other low power short range communications means. The short-range wireless transmitter 29 (e.g., a BLUETOOTH transmitter) receives information from the microprocessor and transmits this information in the form of a packet through an antenna. An external laptop computer or hand-held device 45 features a similar antenna coupled to a matched wireless, short-range receiver that receives the packet. In certain embodiments, the hand-held device is a cellular telephone 50 with a Bluetooth circuit integrated directly into a chipset used in the cellular telephone. In this case, the cellular telephone may include a software application that receives, processes, and displays the information. The secondary wireless component may also include a long-range wireless transmitter that transmits information over a terrestrial, satellite, or 802.11-based wireless network 70. Suitable networks include those operating at least one of the following protocols: CDMA, GSM, GPRS, Mobitex, DataTac, iDEN, and analogs and derivatives thereof. Alternatively, the handheld device is a pager or PDA.

A general method is as follows. The light source 35 transmits light through the skin of the user. The photo-detector 36 detects the light. The pulse rate is determined by the signals received by the photo-detector 36.

This information is sent to the microprocessor for creation of user's pleth waveform. The microprocessor further processes the information to display the pleth waveform. The information is displayed on a display member or an electro-optical display. A plurality of premature atrial contraction events are preferably recorded in a memory of the mobile plethysmographic device 20 and accumulated for statistical purposes for display on the mobile device or on a remote device transmitted via a transceiver of the mobile plethysmographic device 20.

The mobile plethysmographic device 20 alternatively downloads the information to a remote computer for further processing and storage of information. The download may be wireless 70 or through a cable connection.

Figure 10:
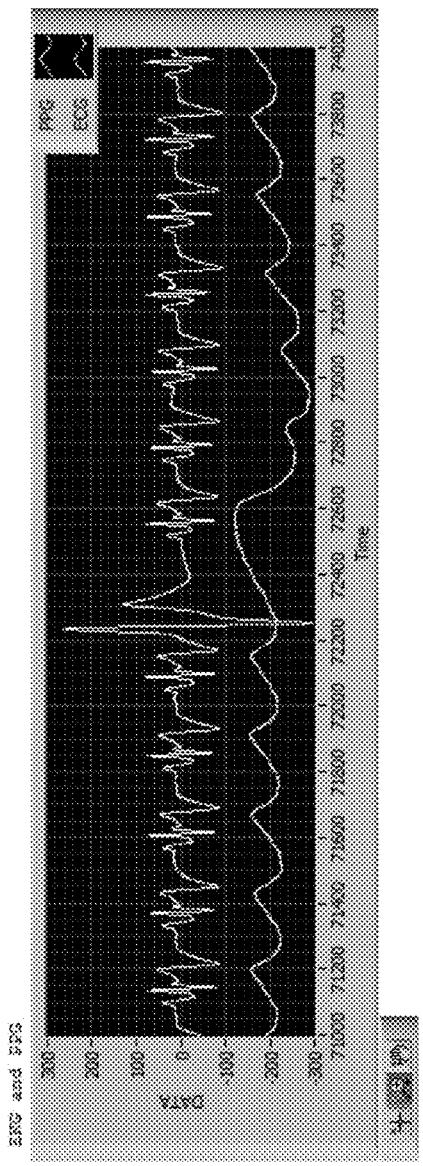
FIG. 10 is a graph of time versus amplitude for a PPG and ECG.

FIG. 10 illustrates a graph 105 of a PPG 110 and ECG 115. A portion of the PPG 110 is further shown in FIG. 12. The PPG is generated by the mobile plethysmographic device 20.

Figure 10A:
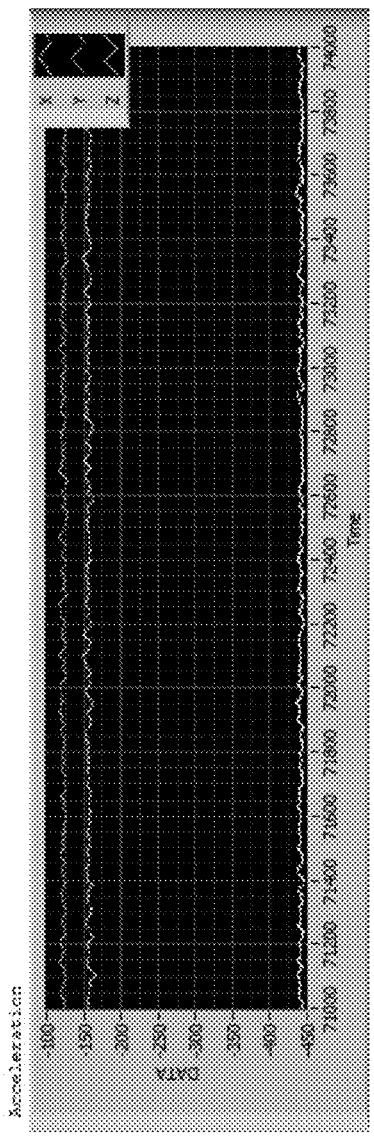
FIG. 10A is a graph of motion over the same time period as the graph of FIG. 10, with the motion detected by an X, Y, and Z accelerometer on the mobile plethysmographic device.

FIG. 10A illustrates a graph 120 of motion detected by an X 121, Y 122, and Z 123 accelerometer. A motion sensor is included to assist in identifying motion noise and filtering the noise from the signal sent by the sensor 30. The motion sensor, such as an accelerometer, is integrated into the circuitry and software of the mobile plethysmographic device 20. As the motion sensor detects an arm swinging, the noise component is utilized with the signal processing noise filtering techniques to provide additional filtering to remove the noise element and improve the accuracy of the mobile plethysmographic device 20. More specifically, the signal from the optical sensor 30 is transmitted to a custom adaptive filter before being sent to a heart beat tracking system and then transmitted to a heart rate beat output. The heart rate beat output provides feedback to the custom adaptive filter, which also receives input from the motion sensor.

In one embodiment, a first systolic pulse peak and a second systolic pulse peak has a first time interval. The amplitude of the first waveform is a measurement from a first valley to the first peak. The amplitude of the second waveform is the measurement from the first valley to the first peak.

Figure 12:
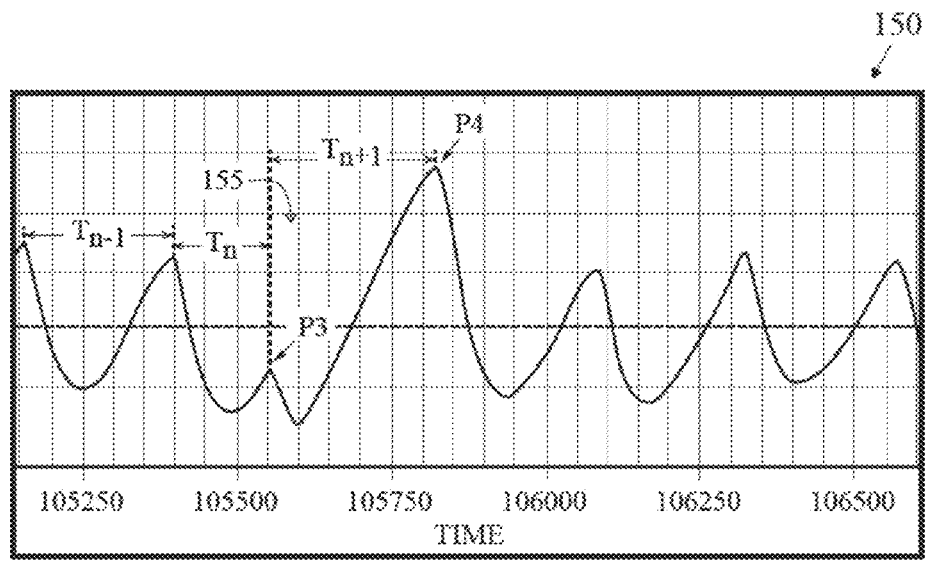
FIG. 12 is a detailed graph of time versus amplitude from FIG. 10 for an example PVC event of a PPG waveform.

FIG. 12 illustrates a graph 150 of an example PVC event as a PPG waveform. As illustrated, a PVC event 155 occurs when time interval between peak P3 and previous peak is shorter than previous time interval and followed by a longer time interval, measured between peaks P3 and P4.

Figure 13:
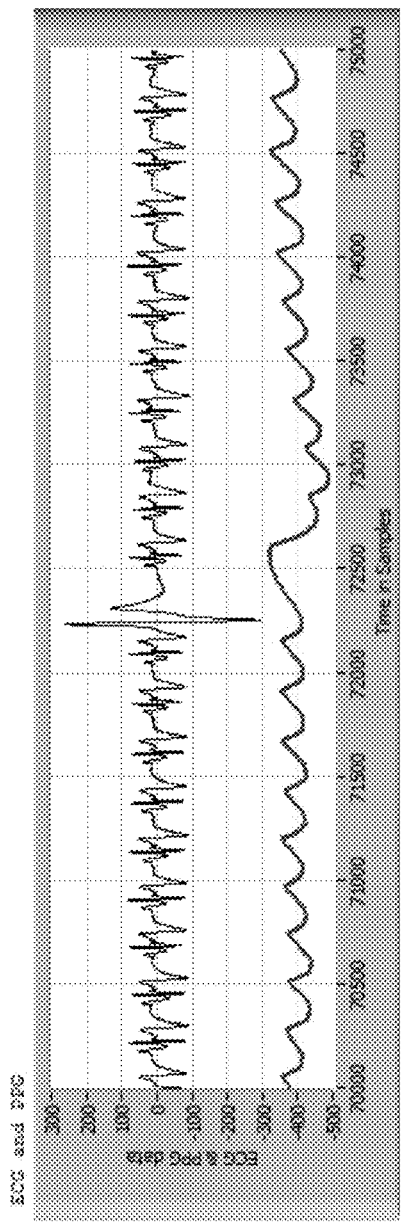
FIG. 13 is a plot graph of time versus amplitude for an example PVC event.
Figure 13A:
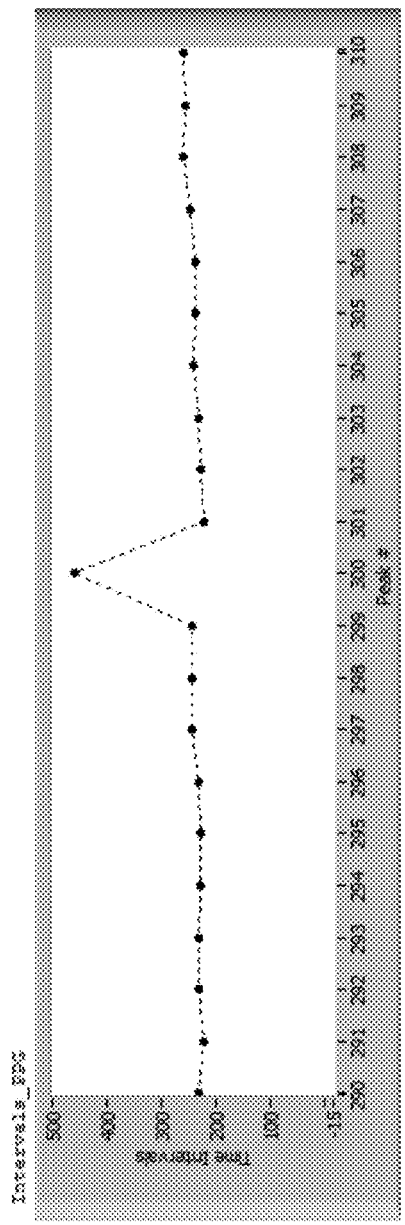
FIG. 13A is a graph illustrating a maximum threshold and a minimum threshold for the peak number.
Figure 14:
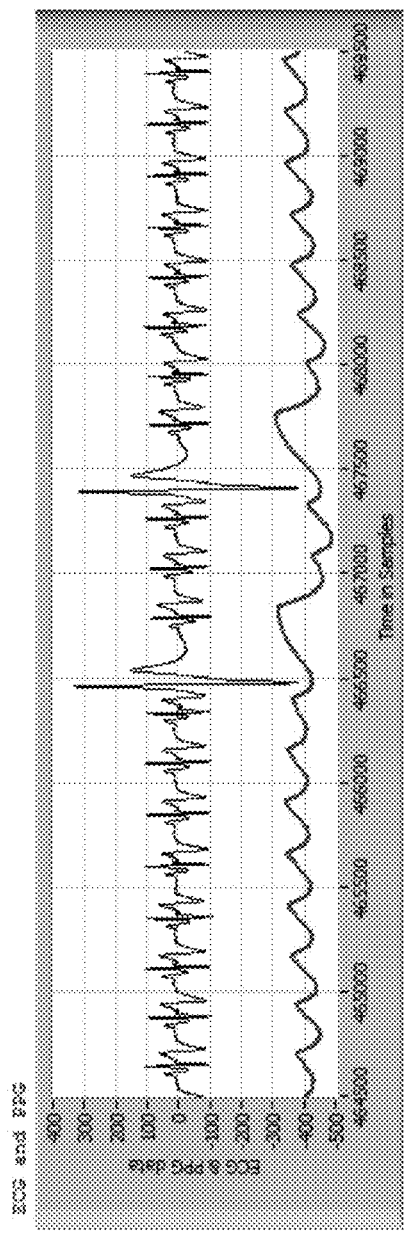
FIG. 14 is a plot graph of time versus amplitude for an example PVC event.
Figure 14A:
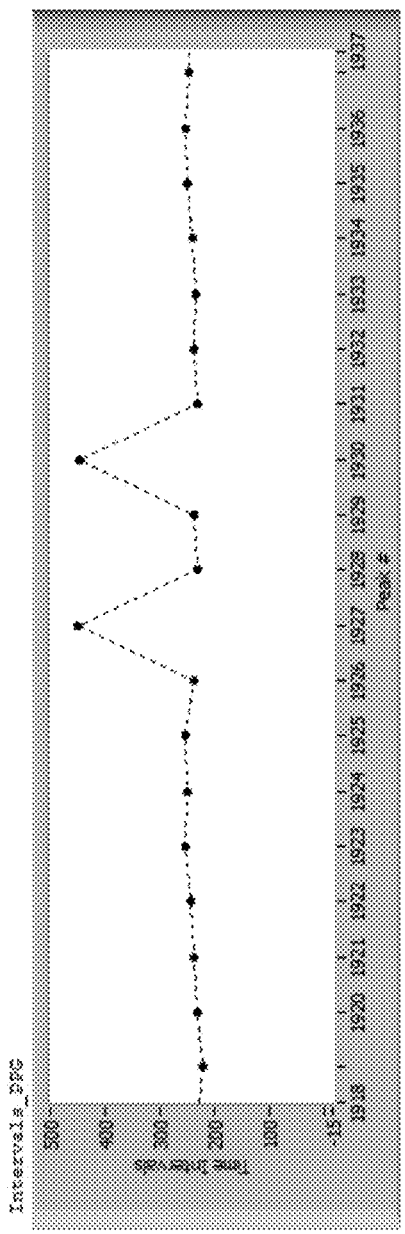
FIG. 14A is a graph illustrating a maximum threshold and a minimum threshold for the peak number.

FIGS. 13 and 14 illustrate plots 160 of an example PVC event as it occurs in the sequence of time intervals between the nearby peaks. As illustrated, a PVC event occurs when a short time interval is followed by a longer time interval, both outside the thresholds. FIGS. 13A and 14A illustrate the maximum threshold and minimum threshold for the time intervals, and illustrates the PVC event, which is a short time interval that occurs outside of the minimum threshold followed immediately by a longer time interval that occurs outside of the maximum threshold.

Figure 11:
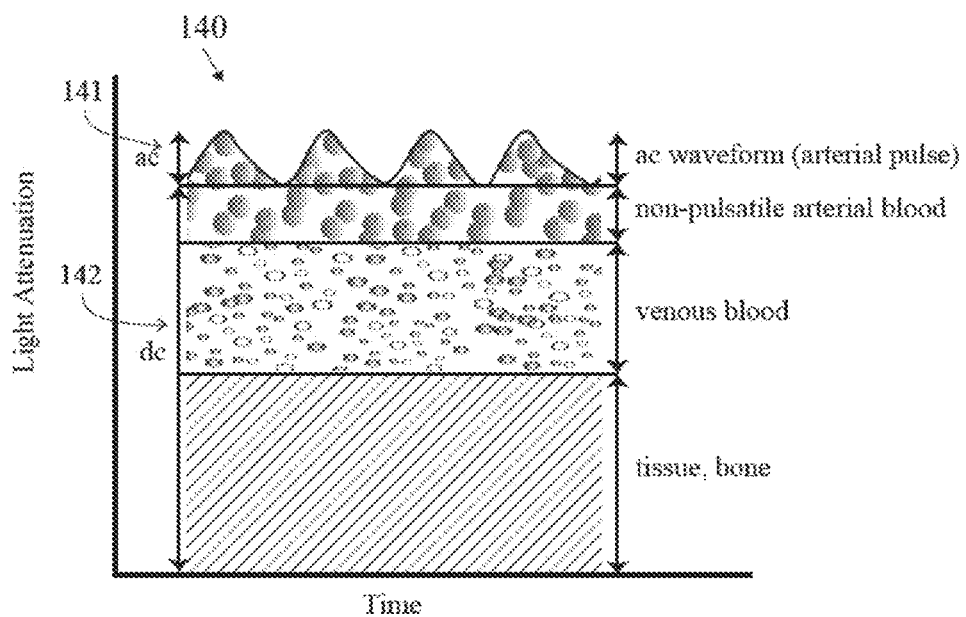
FIG. 11 is a graph of time versus light intensity for a waveform.

When light is applied to a body part, such as the arm 72, a PPG waveform, as shown in FIG. 11, is obtained through reflection of the applied light, the LEDs 35 of the mobile plethysmographic device 20. Photoplethysmographic signals given by the intensity of the LED light received by the photo sensor after it is attenuated in the skin. Total attenuation of the light is composed of a pulsatile component (ac) 141 and nonpulsatile component (dc) 142, as shown in FIG. 11. AC 141 is a change in blood flow, which reflects a change in a blood stream due to heartbeat and related to arterial pulsation, while DC is related to light absorption in the tissue, vein, and diastolic arterial blood volume. The PPG Waveform is obtained by measuring intensity of light after it has been attenuated in the skin. This intensity has an AC compliment that is inverse to the ac attenuation that occurred due to the heartbeat.

The method for determining a premature atrial contraction event for a patient using the mobile plethysmographic device 20 begins with generating a plethysmographic signal. The plethysmographic signal 110, as shown in FIG. 10, for a patient is generated from an optical signal generated by an optical sensor 30 and digitized and processed by a processor, which is then measured. The optical sensor 30 and the processor are on the mobile plethysmographic device 20. The plethysmographic signal 110 comprises multiple pulse waves. A maximum peak value for each pulse wave of the multiple pulse waves of the plethysmographic signal is identified at the processor to generate maximum values of the plethysmographic signal. Time intervals between adjacent maximum values of the plethysmographic signal are calculated at the processor. As shown in FIG. 13A, a threshold minimum time interval and a threshold maximum time interval for the time intervals are established at the processor. As shown in FIG. 12, a premature atrial contraction event for the patient is determined at the processor based on an identification of a time interval that is below the threshold minimum time interval followed immediately by a time interval that is above the threshold maximum tine interval.

The system and method described herein may be used with the mobile plethysmographic device comprising an accelerometer disclosed in Rulkov et al., U.S. Pat. No. 8,579,827 for a Mobile plethysmographic device With An Accelerometer, Method And System, which is hereby incorporated by reference in its entirety.

From the foregoing it is believed that those skilled in the pertinent art will recognize the meritorious advancement of this invention and will readily understand that while the present invention has been described in association with a preferred embodiment thereof, and other embodiments illustrated in the accompanying drawings, numerous changes modification and substitutions of equivalents may be made therein without departing from the spirit and scope of this invention which is intended to be unlimited by the foregoing except as may appear in the following appended claim. Therefore, the embodiments of the invention in which an exclusive property or privilege is claimed are defined in the following appended claims.

We claim as our invention the following:

1. A system for determining a premature ventricular contraction event for a patient, the system comprising:
a mobile plethysmographic device adapted to be worn on a patient, the mobile plethysmographic device comprising a processor, a memory, an optical sensor and an accelerometer, wherein the optical sensor comprises a plurality of green LEDs and a photodetector; and
a display;
wherein the optical sensor is configured to generate an optical signal for the patient through reflection of an applied light from the plurality of green LEDs of the optical sensor and the intensity of the reflected light is received by the photodetector;
wherein the processor is configured to generate a plethysmographic signal for the patient from the optical signal, the plethysmographic signal comprising a plurality of pulse waves;
wherein the processor is configured to identify a maximum peak value for each pulse wave of the plurality of pulse waves of the plethysmographic signal to generate a plurality of maximum values of the plethysmographic signal;
wherein the processor is configured to calculate a plurality of time intervals between adjacent maximum values of the plethysmographic signal;
wherein the processor is configured to establish a threshold minimum time interval and a threshold maximum time interval for the plurality of time intervals; and
wherein the processor is configured to determine a premature ventricular contraction event for the patient based on an identification of a time interval that is above the threshold maximum time interval.

2. The system according to claim 1 wherein the processor is configured to record the premature ventricular contraction event as a first premature ventricular contraction event in a memory of the mobile device.

3. The system according to claim 1 wherein the processor is configured to transmit the premature ventricular contraction event information from the mobile plethysmographic device to a processing device using a transceiver on the mobile plethysmographic device.

4. The system according to claim 1 wherein the processor is configured to monitor for movement of mobile plethysmographic device using an accelerometer to provide a signal for movement of the mobile device.

5. The system according to claim 4 wherein the processor is configured to use three axis accelerometer information from the accelerometer to validate the premature ventricular contraction event by measuring motion activity and verifying the validity of the premature ventricular contraction event when the motion measured by the accelerometer remains less than a preset threshold.

6. The system according to claim 2 wherein the processor is configured to record a plurality of premature ventricular contraction events in the memory of the mobile device and accumulating the plurality of premature ventricular contraction events for statistical purposes for display on the mobile device or on a remote device transmitted via a transceiver of the mobile device.

7. A mobile plethysmographic device for determining a premature ventricular contraction event for a patient, the mobile plethysmographic device comprising:
a processor;
a memory;
an optical sensor comprising a plurality of green LEDs and a photodetector; and
an accelerometer;
wherein the mobile plethysmographic device is adapted to be worn on a patient;
wherein the optical sensor is configured to generate an optical signal for the patient through reflection of an applied light from the plurality of green LEDs of the optical sensor and the intensity of the reflected light is received by the photodetector;
wherein the processor is configured to generate a plethysmographic signal for the patient from the optical signal, the plethysmographic signal comprising a plurality of pulse waves;
wherein the processor is configured to identify a maximum peak value for each pulse wave of the plurality of pulse waves of the plethysmographic signal to generate a plurality of maximum values of the plethysmographic signal;
wherein the processor is configured to calculate a plurality of time intervals between adjacent maximum values of the plethysmographic signal;
wherein the processor is configured to establish a threshold minimum time interval and a threshold maximum time interval for the plurality of time intervals; and
wherein the processor is configured to determine a premature ventricular contraction event for the patient based on an identification of a time interval that is above the threshold maximum time interval.

8. The mobile plethysmographic device according to claim 7 wherein the processor is configured to record the premature ventricular contraction event as a first premature atrial contraction event in a memory of the mobile device.

9. The mobile plethysmographic device according to claim 7 wherein the processor is configured to transmit the premature ventricular contraction event information from the mobile plethysmographic device using a transceiver on the mobile plethysmographic device.

10. The mobile plethysmographic device according to claim 7 wherein the processor is configured to monitor for movement of mobile plethysmographic device using an accelerometer to provide a signal for movement of the mobile device.

11. The mobile plethysmographic device according to claim 10 wherein the processor is configured to use three axis accelerometer information from the accelerometer to validate the premature ventricular contraction event by measuring motion activity and verifying the validity of the premature ventricular contraction event when the motion measured by the accelerometer remains less than a preset threshold.

12. The mobile plethysmographic device according to claim 8 wherein the processor is configured to record a plurality of premature ventricular contraction events in the memory of the mobile device and accumulating the plurality of premature ventricular contraction events for statistical purposes for display on the mobile device or on a remote device transmitted via a transceiver of the mobile device.

* * * * *